US012005154B2

(12) United States Patent
Dellinger

(10) Patent No.: US 12,005,154 B2
(45) Date of Patent: *Jun. 11, 2024

(54) NERVE REPAIR CONDUITS INCORPORATING SILICA FIBERS

(71) Applicant: American Nano, LLC, Clemmons, NC (US)

(72) Inventor: Mitch Dellinger, Clemmons, NC (US)

(73) Assignee: American Nano LLC, Clemmons, NC (US)

( * ) Notice: Subject to any disclaimer, the term of this patent is extended or adjusted under 35 U.S.C. 154(b) by 1159 days.

This patent is subject to a terminal disclaimer.

(21) Appl. No.: 16/660,936

(22) Filed: Oct. 23, 2019

(65) Prior Publication Data

US 2020/0129661 A1 Apr. 30, 2020

Related U.S. Application Data

(60) Provisional application No. 62/750,849, filed on Oct. 26, 2018.

(51) Int. Cl.
| | |
|---|---|
| *A61L 27/02* | (2006.01) |
| *A61L 27/54* | (2006.01) |
| *D01D 5/00* | (2006.01) |
| *D01F 9/08* | (2006.01) |

(52) U.S. Cl.
CPC .............. *A61L 27/025* (2013.01); *A61L 27/54* (2013.01); *D01D 5/0015* (2013.01); *D01F 9/08* (2013.01); *A61L 2300/252* (2013.01); *A61L 2430/32* (2013.01); *D10B 2101/08* (2013.01); *D10B 2509/00* (2013.01)

(58) Field of Classification Search
None
See application file for complete search history.

(56) References Cited

U.S. PATENT DOCUMENTS

| 10,111,783 B1 * | 10/2018 | Dellinger .......... A61F 13/00017 |
| 11,135,806 B2 * | 10/2021 | Dellinger ................. C08K 3/00 |
| 2007/0010831 A1 | 1/2007 | Romero-Ortega et al. |
| 2012/0040581 A1 * | 2/2012 | Kim .................. C04B 35/62259 526/341 |
| 2018/0126038 A1 | 5/2018 | Hyun et al. |

FOREIGN PATENT DOCUMENTS

| CN | 102652903 | 9/2012 |
| CN | 102652903 A * | 9/2012 |

OTHER PUBLICATIONS

Chen et al. Chemically modified electrospun silica nanofibers for promoting growth and differentiation of neural stem cells, J. Mater. Chem. B., 2014, 2, pp. 1205-1215. (Year: 2014).*

(Continued)

*Primary Examiner* — Carlos A Azpuru
*Assistant Examiner* — Casey S Hagopian
(74) *Attorney, Agent, or Firm* — Morgan, Lewis & Bockius LLP

(57) ABSTRACT

Embodiments of the invention include nerve-repair conduits incorporating mats, sheets, and/or powders of silica fibers and methods for producing such conduits. The silica fibers may be formed via electrospinning of a sol gel produced with a silicon alkoxide reagent, such as tetraethyl ortho silicate, alcohol solvent, and an acid catalyst.

34 Claims, 7 Drawing Sheets

(56) References Cited

OTHER PUBLICATIONS

Machine translation of CN-102652903-A, Sep. 5, 2012. (Year: 2012).*
Milea et al. The Influence of Parameters in Silica Sol-gel Process, Bulletin of the Transilvania University of Brasov, Series 1; Engineering Sciences, vol. 4 (53) No. 1, 2011, pp. 59-66. (Year: 2011).*
Wang et al. ("Preparation of Silicon Dioxide Fiber via Sol-Gel Process." Key Engineering Materials, vol. 368-372, Trans Tech Publications, Ltd., Feb. 2008, pp. 794-796. (Year: 2008).*
Qiang Ao, "Progress of nerve bridges in the treatment of peripheral nerve disruptions", Journal of Neurorestoratology, 2016, vol. 4, pp. 107-113.
Chen et al., "Chemically modified electrospun silica nanofibers for promoting growth and differentiation of neural stem cells", Journal of Materials Chemistry B, 2014, vol. 2, pp. 1205-1215.
Choi et al., "Silica Nanofibers From Electrospinning/Sol-Gel Process", Journal of Materials Science Letters, 22, (2003), pp. 891-893.
International Search Report and Written Opinion for International Application No. PCT/US2019-057522, dated Feb. 11, 2020, 15 pages.

\* cited by examiner

NERVE REPAIR CONDUITS INCORPORATING SILICA FIBERS

RELATED APPLICATIONS

This application claims the benefit of and priority to U.S. Provisional Patent Application No. 62/750,849, filed Oct. 26, 2018, the entire disclosure of which is hereby incorporated herein by reference.

TECHNICAL FIELD

In various embodiments, the present invention relates to nerve repair conduits incorporating silica fibers and the use of silica fibers in nerve repair.

BACKGROUND

Nervous system injuries impact tens of thousands of people annually and often result in loss of sensation or motor control, greatly impacting the quality of life of those suffering the injuries. When a nerve is severed due to accident or injury, the first option is often to simply suture the ends of the nerve back together. However, often such procedures cannot be completed without inducing deleterious tensile strain in the nerve. Another nerve-repair option is nerve grafting, in which nerve segments are taken from the injured patient (i.e., autografting), another human donor (i.e., allografting), or a non-human animal (i.e., xenografting) and implanted in the site of the injury to promote axonal regeneration. However, nerve grafting frequently is unsuccessful or only partially successful, resulting in inadequate recovery for the patient.

To address the shortcomings of these approaches, particularly for larger and more extensive nerve injuries, artificial nerve conduits (or "nerve guidance conduits," or simply "nerve conduits") have been developed. Nerve conduits are typically tubular members that enclose the severed ends of an injured nerve and the intervening gap between the ends. The conduit not only guides the recovering nerves physically, but also typically provides a biological and chemical environment that encourages growth and recovery of the nerve. While a host of different materials has been utilized for nerve conduits, at least in experimental trials, patient recovery often remains slow and uncertain, and many nerve injuries fail to recover even when conduits are used. Thus, there is a need for improved nerve conduits that promote the recovery and regrowth of nerves after traumatic injury or degenerative disease.

SUMMARY

In accordance with various embodiments of the present invention, silica fibers, or mats, fragments, gels, or dust (i.e., powder) formed of or including silica fibers are utilized as and/or within artificial nerve conduits. In various embodiments, the silica-fiber material provides large amounts of surface area (e.g., ranging from approximately 50 $m^2$/gram to approximately 100 $m^2$/gram) within and/or on the conduit to promote more extensive and rapid nerve regeneration within the conduit. In various embodiments, mats, sheets, or other porous collections of silica fibers define pores that guide the recovering nerve tissue (e.g., one or more peripheral nerves), thereby facilitating patient recovery. In various embodiments, the nerve conduit itself may include, consist essentially of, or consist of a silica-fiber agent composed of silica fibers and/or one or more mats, sheets, and/or fragments thereof. In other embodiments, the silica-fiber agent may be present within or accompanying a non-silica-fiber-based conduit (e.g., a tubular sheath) in order to promote accelerated healing of the nerve injury.

Nerve conduits in accordance with embodiments of the invention may be positioned at least partially around nerves that are crushed or otherwise injured, partially severed, or fully severed. Thus, in various embodiments, the nerve conduit may surround both the proximal end and the distal end of a transected nerved for promotion of regrowth and recovery thereof. Nerve conduits in accordance with embodiments of the invention may be tubular, with first and second ends sized to receive proximal and distal portions of an injured nerve. In various embodiments, a tubular nerve conduit has an inner diameter (or other parameter, such as width) ranging from, for example, approximately 0.5 mm to approximately 2 cm, although nerve conduits having other sizes may be produced and fall within embodiments of the present invention. The cross-section of the nerve conduit may have any shape, e.g., circular, ovular, polygonal, irregular, etc., and the cross-section may even change along the length of the conduit.

In various embodiments, at least a portion of the nerve conduit may simply include, consist essentially of, or consist of silica fibers, and the regenerating nerve tissue grows within the porosity defined by the intertwined fibers. That is, nerve conduits in accordance with embodiments of the invention are not necessarily tubular, but may define multiple longitudinal channels therethrough (which may be branched and/or sinuous), and/or may be porous scaffolds that bridge at least a portion of the distance between the proximal and distal ends of the damaged nerve.

In some embodiments, the silica fiber-based agent is a non-biodegradable scaffold and/or guide that is not removed from the patient, but becomes integrated with or around the regenerated tissue (e.g., one or more nerves). In accordance with embodiments of the invention, the silica fiber-based agent, when utilized as or with a nerve conduit, acts as a non-biodegradable scaffold that supports nerve tissue healing, regeneration, and/or integrity. Thus, the agent may provide an environment conducive for regeneration and growth of the nerves. In some embodiments, the subject or patient is a mammal. Subjects include veterinary patients such as a dog, cat, or horse, among others. In some embodiments, the patient is a human patient.

In various embodiments, the silica fibers (and/or dust or fragments thereof) are utilized with (e.g., within, on, and/or around) a nerve conduit composed of a different material. For example, all or a portion of the nerve conduit may include, consist essentially of, or consist of one or more biocompatible polymers, e.g., polyesters, polyhydroxyalkonates, proteins, or polysaccharides. Exemplary polyhydroxyalkonates include poly(4-hydroxybutyrate), polyhydroxyvalerate, polyhydroxyhexanoate, polyhydroxyoctanoate, poly(3-hydroxybutyrate), poly(3-hydroxybutyric acid-co-3-hydroxyvaleric acid, and poly(3-hydroxybutyrate-co-3-hydroxyvalerate. Exemplary proteins include silk, collagen, gelatin, fibrinogen, elastin, and keratin. Exemplary polysaccharides include hyaluraonic acid, chitin, chitosan, and alginate. In various embodiments, all or a portion of the nerve conduit may include, consist essentially of, or consist of, for example, silicone, polystyrene, polytetrafluoroethylene, polyglycolic acid, polyvinyl alcohol, or poly(L-lactide-co-ε-caprolactone).

The silica fibers themselves may be produced from a gelatinous material that is electrospun to form a fiber mat. The mat itself (or a portion thereof) may be utilized within or as at least a portion of the nerve conduit, with or without additional processing (e.g., pressing and/or incorporation of an additive material such as a healing agent). In various embodiments, the mat is fragmented into a powder or dust, which may include, consist essentially of, or consist of fibrous fragments. The powder, which may already incorporate one or more additive materials introduced before, during, or after the fiber electrospinning process, may be utilized within or as at least a portion of the nerve conduit. In various embodiments, the powder is mixed with one or more additives for use within or as at least a portion of the nerve conduit. In other embodiments, the powder is pressed or molded into a desired shape (e.g., a tube or a cylinder) and utilized within the nerve conduit, with or without the incorporation of one or more additives.

In various embodiments, the silica fibers may be prepared by electrospinning a sol-gel, which may be prepared with a silicon alkoxide reagent, such as tetraethyl ortho silicate (TEOS), alcohol solvent, and an acid catalyst. In various embodiments, the sol-gel is produced via ripening of sol under controlled environmental conditions, and/or the properties of the sol or sol-gel during the ripening process are monitored, in order to identify various processing windows during which the electrospinning of the sol-gel may be successfully performed. As known in the art, a "sol" is a colloidal solution that gradually evolves towards the formation of a "gel," i.e., a diphasic system containing both a liquid phase and solid phase. Herein, the term "sol-gel" is used to refer to the gel produced from the sol-gel process that may be electrospun into fibers or a fibrous mat.

In various embodiments, the controlled environment for ripening the sol may involve controlled conditions in terms of humidity, temperature, and optionally barometric pressure. For example, the humidity may be controlled within the range of about 30% to about 90%, and the temperature may be controlled within the range of from about 50° F. to about 90° F. By controlling the environmental conditions during ripening, the gel may be electrospun during the time when spinning is optimal, which can occur in a very small window of only several minutes if the ripening process is accelerated by direct heat. When ripening the sol at a constant humidity in the range of about 50% to 80% and a temperature of about 60 to 80° F., the sol will ripen (gelatinize) in a few days, and the window for successful electrospinning may be expanded to at least several hours, and in some embodiments several days. The sol may therefore be ripened in an enclosure which may include one or more environmental monitors, such as a temperature reading device and/or a humidity reading device. Further, gases produced or released by the sol during the ripening process and/or relative weight of the sol may be monitored to determine a suitable or optimal time for electrospinning.

Known processes do not yield silica fiber fibers or mats with sufficient flexibility for many applications, including for applications involving nerve conduits. Instead, many conventional structures are comparatively brittle, rigid, and compact; mats will easily fracture or break; fiber layers are difficult to separate; and generally lack the physical characteristics required for nerve repair. In various embodiments, to achieve a superior material for tissue repair, it is important to electrospin the sol-gel once it is appropriately ripened (or "transitioned"), to achieve a composition with the desired physical characteristics. By transitioning the sol under controlled environmental conditions, and/or monitoring the preparation of the sol-gel during the ripening process, the relatively short window to successfully electrospin the sol-gel can be identified. In accordance with embodiments of the invention, the composition is non-rigid and has a soft texture similar to that of cotton. In various embodiments, silica-fiber compositions electrospun utilizing other conditions and/or that are more brittle or rigid, may be utilized in nerve-conduit embodiments via processing into powder (e.g., fibrous fragments), followed by pressing or molding of the powder into the desired shape. Such powders may have additives, such as one or more healing agents, incorporated therewithin.

Once the sol is adequately ripened into a sol-gel, it is electrospun to form a mat of entangled silica fibers. Once electrospun, the silica fibers may have a variable diameter, such as in the range of from about 50 nm to 5 µm. In some embodiments, the fibers are predominately in the range of about 100 nm to about 2 µm, or predominately in the range of about 200 to about 1000 nm.

For fabrication of the nerve conduit, different materials (e.g., one or more healing agents) may be applied to the silica fibers (or fragments or dust thereof) before, during, and/or after the electrospinning process in order to increase bioactivity and/or promote more rapid nerve growth and healing. For example, nerve growth factor, extracellular matrix protein, glial cell-derived neurotrophic factor, vascular endothelial growth factor, fibroblast growth factor, stem cells, blast cells, epithelial cells, or Schwann cells may be applied to the electrospun or electrospinning silica fibers. Alternatively or in addition, one or more of these materials may be incorporated during and/or after the nerve conduit is implanted within the patient, and/or even one or more times during the nerve growth and regeneration process.

In various embodiments, additives such as one or more healing agents may be incorporated into (e.g., mixed with) powder formed via fragmentation of the electrospun fibers. Such powders may be utilized within, on, and/or as a portion of a nerve conduit, and the powders may be pressed or molded into the proper shape for their deployment within or as a portion of the nerve conduit. Thus, in various embodiments, nerve conduits may incorporate one or more sheets of silica fibers. As utilized herein, a "sheet" of silica fibers refers to an electrospun mat of silica fibers, with or without additional pressing or processing, or to pressed or molded layers (or other shapes, such as cylinders or tubes) of powder (e.g., fibrous fragments) formed via fragmentation of electrospun silica fiber mats.

As utilized herein, in a nerve conduit or silica-fiber composition "incorporating" another material such as one of the various materials listed above and herein (e.g., one or more healing agents) in or on the structure, the material may be bonded to or otherwise adhered to in a substantially solid form, present within the crystalline structure of the fibers or powder particles themselves, and/or present within a mat or sheet (e.g., within pores or spaces between fibers) or within a collection of powder particles as a solid or in liquid form (e.g., in solution with one or more liquid binders or carriers).

In various embodiments of the invention, one or more regions of the nerve conduit include, consist essentially of, or consist of silica fiber powder (with or without an additive such as a healing agent), which may be utilized in powder form and/or pressed or molded into a desired shape. For example, in various embodiments, once a silica fiber mat is successfully electrospun, it may be processed into a powder or dust. For example, the electrospun mat may be "fragmented," i.e., fractured, cut, ground, milled (e.g., in a ball mill or other milling device), pulverized, or otherwise divided into small fragments that maintain a fibrous structure. As used herein, the term "fibrous fragments" (or "fibrous-mat fragments," or simply "fragments") refers to small particles, parts, or flakes of a fibrous mat having an average dimension larger (e.g., 5×, 10×, or even 100×) than the width of at least some of the fibers of the mat. In various embodiments, the average size of a fibrous fragment is in the range of approximately 20 μm to approximately 200 μm. Fibrous fragments may thus resemble microscopic-scale versions of the electrospun mat itself, e.g., intertwined collections of silica fibers, and thus typically are porous and have low densities. Thus, fibrous fragments may be contrasted with other types of micro-scale particles, such as the substantially spherical particles used in colloidal silica, which are each unitary, individual units or grains, rather than small collections of fibers. Various portions of a fibrous fragment (e.g., the edges) may have sharp and/or broken edges resulting from the fracturing process utilized to form the fragments from the electrospun mat. As utilized herein, the terms "silica fiber powder," "silica powder," "silica dust," and "fiber dust" include collections of particles generated via the fragmentation of electrospun fiber mats and/or fibers, and may include fibrous fragments and/or other powder particles resulting from such fragmentation.

Embodiments of the present invention may employ silica fibers, fragments thereof, and/or mixtures incorporating such fibers or fragments, and/or methods for fabricating such fibers or fragments, and/or sols, sol-gels, and/or techniques of forming sols and sol-gels detailed in U.S. patent application Ser. No. 15/934,599, filed on Mar. 23, 2018 (issued as U.S. Pat. No. 10,111,783), U.S. patent application Ser. No. 16/131,531, filed on Sep. 14, 2018, U.S. patent application Ser. No. 16/353,181, filed on Mar. 14, 2019, and U.S. patent application Ser. No. 16/367,313, filed on Mar. 28, 2019, the entire disclosure of each of which is incorporated by reference herein.

In an aspect, embodiments of the invention feature an artificial nerve conduit that includes, consists essentially of, or consists of a tubular polymeric member and a matrix that includes, consists essentially of, or consists of a silica fiber composition. The polymeric member defines a first opening configured to receive a first nerve portion and a second opening configured to receive a second nerve portion. The matrix is disposed within the member between the first and second openings.

Embodiments of the invention may include one or more of the following in any of a variety of combinations. The matrix may include, consist essentially of, or consist of a mat or sheet of silica fibers, and/or a gel, a dust, or a plurality of fibrous fragments derived at least in part from silica fibers. The polymeric member may include, consist essentially of, or consist of a composite or mixture of a polymer material and a dust or plurality of fibrous fragments derived at least in part from silica fibers. The nerve conduit may include, consist essentially of, or consist of (i) a first lateral portion defining the first opening, (ii) a second lateral portion defining the second opening, and (ii) a medial portion disposed between the first and second lateral portions. At least a portion of the matrix may be disposed within the medial portion. The diameter (or other lateral dimension, e.g., width) of the medial portion may be larger than the diameter (or other lateral dimension, e.g., width) of at least one of the first or second lateral portions. The diameter (or other lateral dimension, e.g., width) of the medial portion may be smaller than the diameter (or other lateral dimension, e.g., width) of at least one of the first or second lateral portions. The diameter (or other lateral dimension, e.g., width) of the medial portion may be approximately equal to the diameter (or other lateral dimension, e.g., width) of at least one of the first or second lateral portions.

At least a portion of the matrix may incorporate a healing agent thereon and/or therewithin. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells. At least a portion of the nerve conduit or the polymeric member may incorporate a healing agent thereon and/or therewithin. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells. At least a portion of the polymeric member may include, consist essentially of, or consist of a polyester, a polyhydroxyalkonate, a protein, a polysaccharide, silicone, polystyrene, polytetrafluoroethylene, polyglycolic acid, polyvinyl alcohol, and/or poly(L-lactide-co-ε-caprolactone).

At least a portion of the matrix may be formed at least in part by electrospinning a sol-gel. The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

Producing the sol-gel may include transitioning (or ripening) the initial sol for at least 2 days under conditions where humidity is within the range of about 40% to about 80%, and the temperature is within the range of 50° F. to 90° F. The initial sol may be allowed to transition for at least 3 days, at least 4 days, at least 5 days, at least 6 days, or at least 7 days. The initial sol may be allowed to transition for 2 days to 10 days, and for 2 days to 7 days in some embodiments. The sol-gel may be electrospun when the weight is at from 10% to 60% of the starting weight of the initial sol or sol-gel before ripening (transitioning). The sol-gel may be electrospun when the weight is at from 10% to 40% of the starting weight of the initial sol or sol-gel before ripening (transitioning). The sol-gel may be electrospun when the weight is at from 20% to 40% of the starting weight of the initial sol or sol-gel before ripening (transitioning). The sol-gel may be electrospun when the production of ethylene vapor is 10% to 20% relative to the peak production of ethylene vapors during ripening (transitioning) of the initial sol or sol-gel before ripening. The sol-gel may be electrospun when the production of ethylene vapor therefrom is 10% to 40% relative to the initial sol or sol-gel before ripening (transitioning).

At least a portion of the matrix may be formed by a process including, consisting essentially of, or consisting of (i) electrospinning a sol-gel to form a mat of silica fibers, and (ii) fragmenting the mat to form silica fiber powder. The process of forming the at least a portion of the matrix may include pressing or molding at least a portion of the silica fiber powder. The silica fiber powder may include, consist essentially of, or consist of a plurality of fibrous fragments each composed of a plurality of silica fibers or portions thereof. The fibrous fragments may have an average size between approximately 20 µm and approximately 200 µm. The fibers or portions thereof within the fibrous fragments may have diameters ranging from approximately 50 nm to approximately 5 µm. The fibers or portions thereof within the fibrous fragments may have diameters ranging from approximately 200 nm to approximately 1000 nm.

The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

The process of forming the at least a portion of the matrix may include incorporating a healing agent into the sol-gel before electrospinning thereof, whereby the silica fiber mat comprises the healing agent incorporated therewithin. The process of forming the at least a portion of the matrix may include incorporating a healing agent onto the silica fibers during electrospinning thereof. The process of forming the at least a portion of the matrix may include incorporating a healing agent onto the mat of silica fibers prior to fragmentation thereof. The process of forming the at least a portion of the matrix may include, after fragmentation of the silica fiber mat, incorporating a healing agent onto the silica fiber powder.

In another aspect, embodiments of the invention feature an artificial nerve conduit that includes, consists essentially of, or consists of a tubular member. The member defines a first opening configured to receive a first nerve portion and a second opening configured to receive a second nerve portion. At least a portion of the member includes, consists essentially of, or consists of a silica fiber composition.

Embodiments of the invention may include one or more of the following in any of a variety of combinations. The silica fiber composition may include, consist essentially of, or consist of a mat or sheet of silica fibers. At least a portion of the nerve conduit may be formed at least in part by pressing or molding silica fibers and/or powder derived at least in part from silica fibers. At least a portion of the nerve conduit may include, consist essentially of, or consist of pressed or molded silica fibers and/or pressed or molded powder derived from silica fibers. The nerve conduit may include, consist essentially of, or consist of (i) a first lateral portion defining the first opening, (ii) a second lateral portion defining the second opening, and (ii) a medial portion disposed between the first and second lateral portions. A matrix may be disposed within the medial portion. The diameter (or other lateral dimension, e.g., width) of the medial portion may be larger than the diameter (or other lateral dimension, e.g., width) of at least one of the first or second lateral portions. The diameter (or other lateral dimension, e.g., width) of the medial portion may be smaller than the diameter (or other lateral dimension, e.g., width) of at least one of the first or second lateral portions. The diameter (or other lateral dimension, e.g., width) of the medial portion may be approximately equal to the diameter (or other lateral dimension, e.g., width) of at least one of the first or second lateral portions.

The tubular member may include therewithin a matrix incorporating a healing agent thereon and/or therewithin. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells. At least a portion of the nerve conduit or the tubular member may incorporate a healing agent thereon and/or therewithin. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells. At least a portion of the polymeric member may include, consist essentially of, or consist of a polyester, a polyhydroxyalkonate, a protein, a polysaccharide, silicone, polystyrene, polytetrafluoroethylene, polyglycolic acid, polyvinyl alcohol, and/or poly(L-lactide-co-ε-caprolactone).

At least a portion of the tubular member may be formed at least in part by electrospinning a sol-gel. The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

Producing the sol-gel may include transitioning (or ripening) the initial sol for at least 2 days under conditions where humidity is within the range of about 40% to about 80%, and the temperature is within the range of 50° F. to 90° F. The initial sol may be allowed to transition for at least 3 days, at least 4 days, at least 5 days, at least 6 days, or at least 7 days. The initial sol may be allowed to transition for 2 days to 10 days, and for 2 days to 7 days in some embodiments. The sol-gel may be electrospun when the weight is at from 10% to 60% of the starting weight of the initial sol or sol-gel before ripening (transitioning). The sol-gel may be electrospun when the weight is at from 10% to 40% of the starting weight of the initial sol or sol-gel before ripening (transitioning). The sol-gel may be electrospun when the weight is at from 20% to 40% of the starting weight of the initial sol or sol-gel before ripening (transitioning). The sol-gel may be electrospun when the production of ethylene vapor is 10% to 20% relative to the peak production of ethylene vapors during ripening (transitioning) of the initial sol or sol-gel before ripening. The sol-gel may be electrospun when the production of ethylene vapor therefrom is 10% to 40% relative to the initial sol or sol-gel before ripening (transitioning).

The at least a portion of the member may be formed by a process including, consisting essentially of, or consisting of (i) electrospinning a sol-gel to form a mat of silica fibers, (ii) fragmenting the mat to form silica fiber powder, and (iii) pressing or molding at least a portion of the silica fiber powder. The silica fiber powder may include, consist essentially of, or consist of a plurality of fibrous fragments each composed of a plurality of silica fibers or portions thereof. The fibrous fragments may have an average size between approximately 20 µm and approximately 200 µm. The fibers or portions thereof within the fibrous fragments may have diameters ranging from approximately 50 nm to approximately 5 µm. The fibers or portions thereof within the fibrous fragments may have diameters ranging from approximately 200 nm to approximately 1000 nm.

The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

The process of forming the at least a portion of the tubular member may include incorporating a healing agent into the sol-gel before electrospinning thereof, whereby the silica fiber mat comprises the healing agent incorporated therewithin. The process of forming the at least a portion of the tubular member may include incorporating a healing agent onto the silica fibers during electrospinning thereof. The process of forming the at least a portion of the tubular member may include incorporating a healing agent onto the mat of silica fibers prior to fragmentation thereof. The process of forming the at least a portion of the tubular member may include, after fragmentation of the silica fiber mat, incorporating a healing agent onto the silica fiber powder.

In yet another aspect, embodiments of the invention feature a method of fabricating an artificial nerve conduit. A tubular member is formed from electrospun silica fibers. The tubular member defines a first opening configured to receive a first nerve portion and a second opening configured to receive a second nerve portion.

Embodiments of the invention may include one or more of the following in any of a variety of combinations. Forming the tubular member may include, consist essentially of, or consist of pressing and/or molding the silica fibers and/or powder derived from the silica powders. A healing agent may be incorporated within and/or on at least a portion of the tubular member. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells.

A sol-gel may be electrospun to form a mat of silica fibers, at least a portion of the tubular member being formed from at least a portion of the mat of silica fibers. The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

Producing the sol-gel may include transitioning (or ripening) the initial sol for at least 2 days under conditions where humidity is within the range of about 40% to about 80%, and the temperature is within the range of 50° F. to 90° F. The initial sol may be allowed to transition for at least 3 days, at least 4 days, at least 5 days, at least 6 days, or at least 7 days. The initial sol may be allowed to transition for 2 days to 10 days, and for 2 days to 7 days in some embodiments. The sol-gel may be electrospun when the weight is at from 10% to 60% of the starting weight of the initial sol or sol-gel before ripening (transitioning). The sol-gel may be electrospun when the weight is at from 10% to 40% of the starting weight of the initial sol or sol-gel before ripening (transitioning). The sol-gel may be electrospun when the weight is at from 20% to 40% of the starting weight of the initial sol or sol-gel before ripening (transitioning). The sol-gel may be electrospun when the production of ethylene vapor is 10% to 20% relative to the peak production of ethylene vapors during ripening (transitioning) of the initial sol or sol-gel before ripening. The sol-gel may be electrospun when the production of ethylene vapor therefrom is 10% to 40% relative to the initial sol or sol-gel before ripening (transitioning).

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers after electrospinning thereof.

Forming the tubular member may include, consist essentially of, or consist of (i) electrospinning a sol-gel to form a mat of silica fibers, (ii) fragmenting the mat to form silica fiber powder, and (iii) pressing or molding at least a portion of the silica fiber powder. The silica fiber powder may include, consist essentially of, or consist of a plurality of fibrous fragments each composed of a plurality of silica fibers or portions thereof. The fibrous fragments may have an average size between approximately 20 μm and approximately 200 μm. The fibers or portions thereof within the fibrous fragments may have diameters ranging from approximately 50 nm to approximately 5 μm. The fibers or portions thereof within the fibrous fragments may have diameters ranging from approximately 200 nm to approximately 1000 nm.

The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers prior to fragmentation thereof. A healing agent may be incorporated onto the silica fiber powder after fragmentation of the silica fiber mat.

Embodiments of the invention include artificial nerve conduits fabricated according to any of the methods described above or herein.

In another aspect, embodiments of the invention feature a method of fabricating an artificial nerve conduit. A tubular polymeric member is provided. The tubular polymer member defines a first opening configured to receive a first nerve portion and a second opening configured to receive a second nerve portion. A matrix is disposed within the polymeric member. The matrix includes, consists essentially of, or consists of a silica fiber composition.

Embodiments of the invention may include one or more of the following in any of a variety of combinations. A healing agent may be incorporated (i) within and/or on at least a portion of the matrix and/or (ii) within and/or on at least a portion of the polymeric member. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells. At least a portion of the polymeric member may include, consist essentially of, or consist of a polyester, a polyhydroxyalkonate, a protein, a polysaccharide, silicone, polystyrene, polytetrafluoroethylene, polyglycolic acid, polyvinyl alcohol, and/or poly(L-lactide-co-ε-caprolactone).

The matrix may include, consist essentially of, or consist of a dust, a gel, and/or a plurality of fibrous fragments derived from silica fibers. A sol-gel may be electrospun to form a mat of silica fibers, and the matrix may be formed from at least a portion of the mat of silica fibers. The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

Producing the sol-gel may include transitioning (or ripening) the initial sol for at least 2 days under conditions where humidity is within the range of about 40% to about 80%, and the temperature is within the range of 50° F. to 90° F. The initial sol may be allowed to transition for at least 3 days, at least 4 days, at least 5 days, at least 6 days, or at least 7 days. The initial sol may be allowed to transition for 2 days to 10 days, and for 2 days to 7 days in some embodiments. The sol-gel may be electrospun when the weight is at from 10% to 60% of the starting weight of the initial sol or sol-gel before ripening (transitioning). The sol-gel may be electrospun when the weight is at from 10% to 40% of the starting weight of the initial sol or sol-gel before ripening (transitioning). The sol-gel may be electrospun when the weight is at from 20% to 40% of the starting weight of the initial sol or sol-gel before ripening (transitioning). The sol-gel may be electrospun when the production of ethylene vapor is 10% to 20% relative to the peak production of ethylene vapors during ripening (transitioning) of the initial sol or sol-gel before ripening. The sol-gel may be electrospun when the production of ethylene vapor therefrom is 10% to 40% relative to the initial sol or sol-gel before ripening (transitioning).

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers after electrospinning thereof.

A sol-gel may be electrospun to form a mat of silica fibers. The mat may be fragmented to form silica fiber powder, and at least a portion of the matrix may be formed with the silica fiber powder. At least a portion of the silica fiber powder may be pressed or molded. The silica fiber powder may include, consist essentially of, or consist of a plurality of fibrous fragments each composed of a plurality of silica fibers or portions thereof. The fibrous fragments may have an average size between approximately 20 μm and approximately 200 μm. The fibers or portions thereof within the fibrous fragments may have diameters ranging from approximately 50 nm to approximately 5 μm. The fibers or portions thereof within the fibrous fragments may have diameters ranging from approximately 200 nm to approximately 1000 nm.

The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers prior to fragmentation thereof. A healing agent may be incorporated onto the silica fiber powder after fragmentation of the silica fiber mat.

Embodiments of the invention include artificial nerve conduits fabricated according to any of the methods described above or herein.

In yet another aspect, embodiments of the invention feature a method for improving integrity of an injured nerve in a subject. The injured nerve includes, consists essentially of, or consists of a proximal portion, a distal portion, and an injury site disposed between the proximal and distal portions. The method includes, consists essentially of, or consists of applying an artificial nerve conduit over and/or within the injury site. The artificial nerve conduit includes, consists essentially of, or consists of electrospun silica fibers and/or powder derived therefrom (e.g., pressed or molded into a shaped sheet).

Embodiments of the invention may include one or more of the following in any of a variety of combinations. The injury site may include, consist essentially of, or consist of a gap between the proximal and distal portions of the nerve (e.g., due to a full or partial transection of the nerve). The proximal and distal portions of the nerve may be received within opposing openings defined in the nerve conduit. The injury site may include, consist essentially of, or consist of an injured (e.g., damaged) portion of the nerve between the proximal and distal portions of the nerve. The nerve conduit may be applied around at least a portion of the injury site. The subject may be a mammal. The subject may be a human. The subject may be a veterinary patient, such as a cat, a dog, or a horse.

At least a portion of the nerve conduit may include a healing agent therewithin and/or thereon. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells.

The nerve conduit may be prepared, at least in part, by electrospinning a sol-gel to form a mat of silica fibers. The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

Producing the sol-gel may include transitioning (or ripening) the initial sol for at least 2 days under conditions where humidity is within the range of about 40% to about 80%, and the temperature is within the range of 50° F. to 90° F. The initial sol may be allowed to transition for at least 3 days, at least 4 days, at least 5 days, at least 6 days, or at least 7 days. The initial sol may be allowed to transition for 2 days to 10 days, and for 2 days to 7 days in some embodiments. The sol-gel may be electrospun when the weight is at from 10% to 60% of the starting weight of the initial sol or sol-gel before ripening (transitioning). The sol-gel may be electrospun when the weight is at from 10% to 40% of the starting weight of the initial sol or sol-gel before ripening (transitioning). The sol-gel may be electrospun when the weight is at from 20% to 40% of the starting weight of the initial sol or sol-gel before ripening (transitioning). The sol-gel may be electrospun when the production of ethylene vapor is 10% to 20% relative to the peak production of ethylene vapors during ripening (transitioning) of the initial sol or sol-gel before ripening. The sol-gel may be electrospun when the production of ethylene vapor therefrom is 10% to 40% relative to the initial sol or sol-gel before ripening (transitioning).

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers after electrospinning thereof.

The nerve conduit may be prepared, at least in part, by (i) electrospinning a sol-gel to form a mat of silica fibers, (ii) fragmenting the mat to form silica fiber powder, and (iii) pressing or molding at least a portion of the silica fiber powder. The silica fiber powder may include, consist essentially of, or consist of a plurality of fibrous fragments each composed of a plurality of silica fibers or portions thereof. The fibrous fragments may have an average size between approximately 20 µm and approximately 200 µm. The fibers or portions thereof within the fibrous fragments may have diameters ranging from approximately 50 nm to approximately 5 µm. The fibers or portions thereof within the fibrous fragments may have diameters ranging from approximately 200 nm to approximately 1000 nm.

The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers prior to fragmentation thereof. A healing agent may be incorporated onto the silica fiber powder after fragmentation of the silica fiber mat.

In another aspect, embodiments of the invention feature a method for improving integrity of an injured nerve in a subject. The injured nerve includes, consists essentially of, or consists of a proximal portion, a distal portion, and an injury site disposed between the proximal and distal portions. A tubular polymeric member is provided. The tubular polymeric member defines a first opening configured to receive the proximal portion and a second opening configured to receive the distal portion. A matrix is disposed within the member between the first and second openings. The matrix includes, consists essentially of, or consists of a silica fiber composition. The proximal portion of the nerve is disposed within the first opening. The distal portion of the nerve is disposed within the second opening. The matrix is disposed between (and may be in direct contact with) the proximal and distal portions of the nerve.

Embodiments of the invention may include one or more of the following in any of a variety of combinations. The matrix may include, consist essentially of, or consist of a mat or sheet of silica fibers, and/or a gel, a dust, or a plurality of fibrous fragments derived from silica fibers. At least a portion of the matrix may incorporate a healing agent thereon and/or therewithin. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells. At least a portion of the polymeric member may incorporate a healing agent thereon and/or therewithin. The healing agent may include, consist essentially of, or consist of a growth factor, a matrix protein, and/or a plurality of cells. The healing agent may include, consist essentially of, or consist of nerve growth factor, extracellular matrix protein, glial cell-derived neurotrophic factor, vascular endothelial growth factor, fibroblast growth factor, stem cells, blast cells, epithelial cells, and/or Schwann cells. At least a portion of the polymeric member may include, consist essentially of, or consist of a polyester, a polyhydroxyalkonate, a protein, a polysaccharide, silicone, polystyrene, polytetrafluoroethylene, polyglycolic acid, polyvinyl alcohol, and/or poly(L-lactide-co-ε-caprolactone). The subject may be a mammal. The subject may be a human. The subject may be a veterinary patient, such as a cat, a dog, or a horse.

At least a portion of the matrix may be prepared, at least in part, by electrospinning a sol-gel to form a mat of silica fibers. The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

Producing the sol-gel may include transitioning (or ripening) the initial sol for at least 2 days under conditions where humidity is within the range of about 40% to about 80%, and the temperature is within the range of 50° F. to 90° F. The initial sol may be allowed to transition for at least 3 days, at least 4 days, at least 5 days, at least 6 days, or at least 7 days. The initial sol may be allowed to transition for 2 days to 10 days, and for 2 days to 7 days in some embodiments. The sol-gel may be electrospun when the weight is at from 10% to 60% of the starting weight of the initial sol or sol-gel before ripening (transitioning). The sol-gel may be electrospun when the weight is at from 10% to 40% of the starting weight of the initial sol or sol-gel before ripening (transitioning). The sol-gel may be electrospun when the weight is at from 20% to 40% of the starting weight of the initial sol or sol-gel before ripening (transitioning). The sol-gel may be electrospun when the production of ethylene vapor is 10% to 20% relative to the peak production of ethylene vapors during ripening (transitioning) of the initial sol or sol-gel before ripening. The sol-gel may be electrospun when the production of ethylene vapor therefrom is 10% to 40% relative to the initial sol or sol-gel before ripening (transitioning).

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers after electrospinning thereof.

At least a portion of the matrix may be prepared, at least in part, by (i) electrospinning a sol-gel to form a mat of silica fibers and (ii) fragmenting the mat to form silica fiber powder. At least a portion of the silica fiber powder may be pressed or molded. The silica fiber powder may include, consist essentially of, or consist of a plurality of fibrous fragments each composed of a plurality of silica fibers or portions thereof. The fibrous fragments may have an average size between approximately 20 µm and approximately 200 µm. The fibers or portions thereof within the fibrous fragments may have diameters ranging from approximately 50 nm to approximately 5 µm. The fibers or portions thereof within the fibrous fragments may have diameters ranging from approximately 200 nm to approximately 1000 nm.

The sol-gel may be prepared with tetraethylorthosilicate (TEOS). The sol-gel may be produced from an initial sol containing 75% to 90% TEOS, 8% to 25% ethanol, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may contain 70% to 90% TEOS by weight, 8% to 25% ethanol by weight, an acid catalyst, and the balance water. The initial sol may include, consist essentially of, or consist of 70% to 90% TEOS by weight, 8% to 25% ethanol by weight, an acid catalyst, and water. The initial sol may include, consist essentially of, or consist of 70% to 90% TEOS by weight, 8% to 25% ethanol by weight, 1% to 10% water by weight, and the acid catalyst. The initial sol may include, consist essentially of, or consist of 75% to 85% by weight TEOS, 12% to 20% by weight ethanol, and about 2% to 5% by weight water. The initial sol may include, consist essentially of, or consist of about 80% by weight TEOS, about 17% by weight ethanol, and about 3% by weight water. The acid catalyst may include, consist essentially of, or consist of HCl. The initial sol may contain less than about 0.1% of the acid catalyst by weight. The initial sol may contain from 0.02% to 0.08% of the acid catalyst by weight. The initial sol may contain one or more reagents that alter one or more properties of the initial sol, the sol-gel, and/or the silica fibers.

A healing agent may be incorporated into the sol-gel before electrospinning thereof, whereby the silica fiber mat comprises the healing agent incorporated therewithin. A healing agent may be incorporated onto the silica fibers during electrospinning thereof. A healing agent may be incorporated onto the mat of silica fibers prior to fragmentation thereof. A healing agent may be incorporated onto the silica fiber powder after fragmentation of the silica fiber mat.

These and other objects, along with advantages and features of the present invention herein disclosed, will become more apparent through reference to the following description, the accompanying drawings, and the claims. Furthermore, it is to be understood that the features of the various embodiments described herein are not mutually exclusive and may exist in various combinations and permutations. As used herein, the terms "approximately," "about," and "substantially" mean ±10%, and in some embodiments, ±5%. The term "consists essentially of" means excluding other materials that contribute to function, unless otherwise defined herein. Nonetheless, such other materials may be present, collectively or individually, in trace amounts. Unless otherwise indicated, nerve conduits, materials, mixtures, regions, and other structures described herein may incorporate unintentional impurities.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention. In the following description, various embodiments of the present invention are described with reference to the following drawings, in which.

DETAILED DESCRIPTION

Figure 1A:
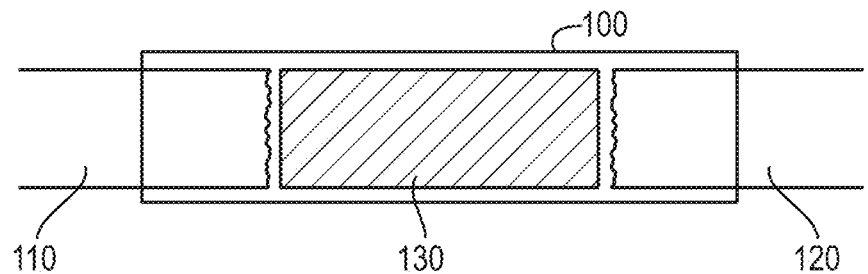
FIGS. 1A-1D are cross-sectional schematics of nerve conduits in accordance with embodiments of the present invention.

In various embodiments of the present invention, nerve conduits, or portions thereof, are fabricated utilizing layers (or "mats") or sheets of silica fibers, other collections of the fibers, and/or dust and/or fragments and/or gels of such fibers. Various silica-fiber compositions utilized as and/or within nerve conduits in accordance with embodiments of the invention incorporate other materials mixed with, applied to, and/or incorporated within the silica fibers in order to facilitate tissue (e.g., nerve) healing. The silica fibers themselves may be produced from a gelatinous material that is electrospun to form a fiber mat. The mat itself (or a portion thereof) may be utilized as and/or within the nerve conduit, with or without additional processing (e.g., pressing, molding, and/or incorporation of an additive material). In various embodiments, the mat is fragmented into a powder or dust, which may include, consist essentially of, or consist of fibrous fragments. The powder, which may already incorporate one or more additive materials introduced before, during, or after the fiber electrospinning process, may be utilized in and/or as all or a portion of the nerve conduit. In various embodiments, the powder is mixed with one or more additives for use in and/or as at least a portion of the nerve conduit. In other embodiments, the powder is pressed or molded into a desired shape (e.g., tube or cylinder) and utilized in or as at least a portion of the nerve conduit, with or without the incorporation of one or more additives.

In some embodiments, silica fibers and/or fiber mats are electrospun from a gelatinous material. For example, the silica fibers and/or fiber mats may be prepared by electrospinning a sol-gel, which may be prepared with a silicon alkoxide reagent, such as tetraethyl ortho silicate (TEOS), alcohol solvent, and an acid catalyst.

In some embodiments, the sol-gel for preparing the silica fiber composition is prepared by a method that includes preparing a first mixture containing an alcohol solvent, a silicon alkoxide reagent such as tetraethylorthosilicate (TEOS); preparing a second mixture containing an alcohol solvent, water, and an acid catalyst; fully titrating the second mixture into the first mixture; and processing (ripening) the combined mixture to form a gel for electrospinning. In some embodiments, the silicon alkoxide reagent is TEOS. Alternative silicon alkoxide reagents include those with the formula $Si(OR)_4$, where R is from 1 to 6, and preferably 1, 2, or 3.

In some embodiments, the sol comprises, consists essentially of, or consists of about 70% to about 90% by weight silicon alkoxide (e.g., TEOS), about 5% to about 25% by weight alcohol solvent (e.g., anhydrous ethanol), an acid catalyst (e.g., less than about 0.1% by weight when using HCl) and water. Any sol or sol-gel described herein may include the balance water (i.e., water may constitute any amount of the sol or sol-gel that is otherwise unspecified). Any sol or sol-gel described herein may optionally contain one or more reagents or additives that may or do alter one or more properties of the sol, the sol-gel, and/or the silica fibers (and/or powder prepared therefrom). Such reagents may include, but are not limited to, for example, polymers and polymeric solutions, inert reagents, alcohols, organic and/or aqueous solvents, organic salts, inorganic salts, metals, metal oxides, metal nitrides, metal oxynitrides, carbon (e.g., graphene, graphite, amorphous carbon, fullerenes, etc.), etc.

In some embodiments, the sol contains 70% to 90% tetraethyl orthosilicate (TEOS) by weight, 8% to 25% ethanol by weight, 1% to 10% water by weight, and an acid catalyst. In some embodiments, the sol contains 75% to 85% by weight TEOS, 12% to 20% by weight ethanol, and about 2% to 5% by weight water. An exemplary sol contains about 80% by weight TEOS, about 17% by weight ethanol, and about 3% by weight water. In some embodiments, the acid catalyst is HCl. For example, the sol may contain less than about 0.1% HCl by weight. For example, the sol may contain from 0.02% to 0.08% HCl by weight. In various embodiments, the sol does not contain an organic polymer, or other substantial reagents, such that the fiber composition will be substantially pure $SiO_2$. In various embodiments, the sol does not include inorganic salts (e.g., sodium chloride, lithium chloride, potassium chloride, magnesium chloride, calcium chloride, and/or barium chloride), nor are, in various embodiments, inorganic salts mixed with other components of the sol or into the sol itself. In various embodiments, the fiber composition does not include metals or metal oxides (e.g., $TiO_2$ or $ZrO_2$). In various embodiments, the fiber composition consists essentially of $SiO_2$, i.e., contains only $SiO_2$ and unintentional impurities, and, in some embodiments, species and/or complexes resulting from the incomplete conversion of the sol to $SiO_2$ (e.g., water and/or chemical groups such as ethoxy groups, silanol groups, hydroxyl groups, etc.). In various embodiments, additives may be incorporated onto silica fibers and or powder prepared therefrom after the electrospinning process.

In some embodiments, the alcohol solvent is an anhydrous denatured ethanol, or in some embodiments, methanol, propanol, butanol or any other suitable alcohol solvent. The first mixture may be agitated, for example, using a magnetic stirrer, vibration platform or table, or other agitation means. The second mixture contains an alcohol solvent, water, and an acid catalyst. The alcohol solvent may be an anhydrous denatured alcohol, or may be methanol, propanol, butanol or any other suitably provided alcohol solvent. Water may be distilled water or deionized water. Enough acid catalyst is added to the mixture to aid in the reaction. This acid catalyst may be hydrochloric acid, or may be sulfuric acid or other suitable acid catalyst. The second mixture may be agitated, for example, magnetic stirrer, vibration platform or table, or other agitation means. In some embodiments, the first mixture (or sol) and the second mixture (or sol) are created without the use of direct heat (i.e., heat applied via extrinsic means such as a hot plate or other heat source).

According to various embodiments, the first mixture and the second mixture are combined by dripping or titrating the second mixture into the first mixture, preferably with agitation. The combined mixture is then further processed by allowing the sol to ripen in a controlled environment until a substantial portion of the alcohol solvent has evaporated to create a sol-gel suitable for electrospinning. For example, the controlled environment may include an enclosure with at least one vent and optionally a fan to draw gases away from the mixture, and which may involve controlled conditions in terms of humidity, temperature, and optionally barometric pressure. For example, the humidity may be controlled (e.g., via use of conventional humidifiers and/or dehumidifiers) within the range of about 30% to about 90%, such as from about 40% to about 80%, or in some embodiments, from about 50% to about 80%, or from about 50% to about 70% (e.g., about 55%, or about 60%, or about 65%). Some humidity may be helpful to slow evaporation of solvent, and thereby lengthen the window for successful electrospinning. In some embodiments, the temperature is in the range of from about 50° F. to about 90° F., such as from about 60° F. to about 80° F., or from about 65° F. to about 75° F. In various embodiments, the sol is not exposed to heat over 150° F. or heat over 100° F., so as to avoid accelerating the transition. In some embodiments, barometric pressure is optionally controlled (e.g., using a low pressure vacuum source such as a pump or a fan). By controlling the environmental conditions during ripening, the time period during which the gel may be electrospun may be lengthened; this time period may be a small window of only several minutes if the ripening process is too accelerated, such as with direct heat. When ripening the sol at a constant humidity of about 55% and temperature of about 72° F., the sol will ripen (gelatinize) in a few days, and the window for successful electrospinning may be expanded to at least several hours, and in some embodiments several days. In various embodiments, the ripening process takes at least 2 days, or at least 3 days in some embodiments. However, in various embodiments the ripening does not take more than 10 days, or more than 7 days. In some embodiments, the ripening process takes from 2 to 10 days, or from 2 to 7 days, or from 2 to 5 days, or from 2 to 4 days (e.g., about 2, about 3, or about 4 days). In various embodiments, the sol-gel is spinnable well before it transitions into a more solidified, non-flowable mass.

The enclosure space for ripening the sol-gel may include a vent on at least one surface for exhausting gases from within the enclosure, and optionally the vent may include a fan for exhausting gases produced during the ripening process. The enclosure space may optionally include a heating source (e.g., one or more heating elements, for example resistive heating elements) for providing a nominal amount of heat within the enclosure space, to maintain a preferred temperature. In some embodiments, a source of humidity (e.g., an open container of water or other aqueous, water-based liquid) is provided within the enclosure environment to adjust the humidity to a desired range or value. The enclosure may further include one or more environmental monitors, such as a temperature reading device (e.g., a thermometer, thermocouple, or other temperature sensor) and/or a humidity reading device (e.g., a hygrometer or other humidity sensor).

In some embodiments, the sol-gel is electrospun after a ripening process of at least 2 days, or at least 36 hours, or at least 3 days, or at least 4 days, or at least 5 days at the controlled environmental conditions (but in various embodiments, not more than 10 days or not more than 7 days under the controlled environmental conditions). By slowing the ripening process, the ideal time to spin the fibers may be identified. The weight of the sol-gel may be used as an indicator of when the sol-gel is at or near the ideal time to electrospin. Without intending to be bound by theory, it is believed that the viscosity of the sol-gel is a poor determinant for identifying the optimal time for electrospinning. For example, in various embodiments, the sol-gel is from about 10% to about 60% of the original weight of the sol (based on loss of alcohol solvent during transitioning). In some embodiments, the sol-gel is from 15 to 50% of the original weight of the sol, or in the range of about 20 to about 40% of the original weight of the sol.

In some embodiments, the sol-gel is ripened for at least 2 days, or at least 36 hours, or at least 3 days, or at least 4 days, or at least 5 days, and is electrospun when the ethylene vapors produced by the composition are between about 10% and about 40% of the vapors produced by the starting sol, such as in the range of about 10% and about 25%, or in the range of about 10% to about 20%. Ethylene is a colorless flammable gas with a faint sweet and musky odor (which is clearly evident as solvent evaporation slows). Ethylene is produced by the reaction of ethanol and acid. Ethylene may optionally be monitored in the vapors using a conventional ethylene monitor. In other embodiments, gases produced by the sol during the sol ripening process are monitored to determine a suitable or optimal time for electrospinning. Gas profiles may be monitored using gas chromatography.

In various embodiments, additives such as one or more healing agents may be introduced into the sol-gel prior to electrospinning, and such additives may therefore be incorporated into and/or onto the spun fibers. In various embodiments, the additive is introduced into the sol-gel immediately prior to (e.g., less than 0.5 hour before, less than 1 hour before, less than 2 hours before, or less than 5 hours before) electrospinning so that the sol-gel successfully ripens prior to introduction of the additive, facilitating successfully electrospinning. In various embodiments, the additive may be introduced into the sol-gel after it has ripened for at least 0.5 days, at least 1 day, at least 2 days, or at least 3 days.

Silica fiber mats and compositions produced in accordance with embodiments of the present invention exhibit one or more beneficial properties when compared to fiber compositions spun at non-optimal times (e.g., with inadequate ripening of the sol-gel). For example, fiber mats and compositions in accordance with embodiments of the invention do not burn, char, or visibly degrade upon direct application of heat or open flame. In contrast, various fiber compositions spun at non-optimal times will exhibit charring and/or visible color change when exposed to sufficient heat or open flame. Moreover, fiber mats and compositions in accordance with embodiments of the invention effectively wick moisture (e.g., water or bodily fluids), absorbing such fluid into the fiber mat. In contrast, various fiber compositions spun at non-optimal times will not visibly absorb or wick moisture even when directly applied thereto; such compositions tend to be hydrophobic. Finally, fiber mats and compositions in accordance with embodiments of the invention are fluffy and may be easily shaped to uneven, non-uniform, and/or non-planar (e.g., curved) surfaces or shapes without fracturing or loss of structural integrity; thus, such compositions may be readily applied to or conformed to a variety of different surfaces and/or tissues such as nerves or nerve ends. In contrast, various fiber compositions spun at non-optimal times tend to be flat, plate-like, brittle, and will at least partially fracture if excessively mechanically shaped or bent.

Thus, in various embodiments, when the sol-gel is ripened as detailed herein, the resulting silica fibers and silica fiber mats are advantageously flexible. The mats may also be folded, wrapped, or otherwise deformed in order to conform to a specific desired shape or within nerve conduits having a variety of shapes and sizes. In various embodiments, sol-gels ripened for an inadequate amount of time may result in silica fibers that are more brittle and that tend to fragment upon mechanical deformation.

In various embodiments, the sol-gel may be ripened for a shorter period of time, as long as the sol-gel remains spinnable via electrospinning. The resulting silica fiber mat or collection of fibers may in some cases be more brittle after ripening for a shorter time period, but such brittleness may not prevent the fragmenting of the fibers and production of powder therefrom. In various embodiments, silica fiber powder utilized in or as at least a portion of the nerve conduit may be produced from silica fibers or fiber mats electrospun after ripening for less time than silica fibers or mats utilized within or as at least a portion of the nerve conduit in mat or sheet form. For example, silica fiber powder utilized in or as at least a portion of the nerve conduit (e.g., after optional pressing or molding) may be produced from silica fibers or fiber mats electrospun after ripening for less than 2 days or less than 1 day.

The processing of the sol-gel mixture may require stirring or other agitation of the mixtures at various intervals or continuously due to the development of silicone dioxide crystalline material on the top surface of the mixtures. This development of crystalline material on the top surface slows the processing time and it is believed that the crystalline material seals off exposure of the mixture to the gaseous vacuum provided within the enclosure space. In some embodiments, any solid crystalline material is removed from the mixture.

Upon completion of the sol-gel process, the sol-gel is then electrospun using any known technique. The sol or sol-gel may be preserved (e.g., frozen or refrigerated) if needed (and such time generally will not apply to the time for ripening). An exemplary process for electrospinning the sol-gel is described in Choi, Sung-Seen, et al., Silica nanofibers from electrospinning/sol-gel process, *Journal of Materials Science Letters* 22, 2003, 891-893, which is hereby incorporated by reference in its entirety. Exemplary processes for electrospinning are further disclosed in U.S. Pat. No. 8,088,965, which is hereby incorporated by reference in its entirety.

In an exemplary electrospinning technique, the sol-gel is placed into one or more syringe pumps that are fluidly coupled to one or more spinnerets. The spinnerets are connected to a high-voltage (e.g., 5 kV to 50 kV) source and are external to and face toward a grounded collector drum. The drum rotates during spinning, typically along an axis of rotation approximately perpendicular to the spinning direction extending from the spinnerets to the drum. As the sol-gel is supplied to the spinnerets from the syringe pumps (or other holding tank), the high voltage between the spinnerets and the drum forms charged liquid jets that are deposited on the drum as small entangled fibers. As the drum rotates and electrospinning continues, a fibrous mat of silica fibers is formed around the circumference of the drum. In various embodiments, the spinnerets and syringe pump(s) may be disposed on a movable platform that is movable parallel to the length of the drum. In this manner, the length along the drum of the resulting fiber mat may be increased without increasing the number of spinnerets. The diameter of the drum may also be increased to increase the areal size of the electrospun mat. The thickness of the mat may be largely dependent upon the amount of sol-gel used for spinning and thus the amount of electrospinning time. For example, the mat may have a thickness of greater than about ⅛ inch, or greater than about ¼ inch, or greater than about ⅓ inch, or greater than about ½ inch.

In various embodiments, the fibers of an electrospun collection of silica fibers or fiber mat are preferentially oriented in a particular direction. In example embodiments, the use of silica fibers substantially oriented (e.g., within ±2°, ±5°, ±10°, or ±20°) along the longitudinal direction (i.e., the direction from the proximal end of the damaged nerve to the distal end), either as all or a portion of the nerve conduit or within the nerve conduit, may beneficially accelerate nerve regeneration and healing. The electrospinning of substantially oriented fibers may be performed by one of skill in the art without undue experimentation. For example, as detailed in U.S. Pat. No. 7,993,567, filed Jun. 2, 2008, the entire disclosure of which is incorporated by reference herein, the electrospinning apparatus may incorporate one or more auxiliary electrodes proximate the collector drum and, e.g., opposite the dispensing spinneret(s). Such electrodes may shape the electric field proximate the collector drum such that the electrospun fibers are deposited with a preferred orientation rather than as a random mat. The oriented fibers may then be utilized to form all or a portion of a nerve conduit with the fiber orientation aligned to a desired dimension of the conduit (e.g., along the longitudinal direction or axial dimension of the conduit).

After completion of the electrospinning process, the resulting mat is removed from the drum. For example, the mat may be cut and peeled away from the drum in one or more pieces. The mat may then be fragmented to form a powder. In various embodiments, the powder includes, consists essentially of, or consists of small fibrous fragments that are each intertwined collections of silica fibers, rather than unitary solid particles. In some embodiments, the electrospun mat may be fractured, cut, ground, milled, or otherwise divided into small fragments that maintain a fibrous structure. In some embodiments, the mat (or one or more portions thereof) is rubbed through one or more screens or sieves, and the mesh size of the screen determines, at least in part, the size of the resulting fibrous fragments or powder or dust produced from the electrospun mat. For example, the mat or mat portions may be rubbed through a succession of two or more screens having decreasing mesh sizes (e.g., screens having mesh numbers of 100, 200, 300, or even 400), in order to produce a powder or dust or collection of fibrous fragments having the desired sizes.

In various embodiments, one or more healing factors or other agents or additives are introduced onto the silica fibers during the electrospinning process. For example, a liquid or solution containing the material (e.g., in liquid or encapsulated form) may be sprayed or misted onto the fibers between the spinnerets and the drum or as formed on the drum itself. In various embodiments, the solution contains one or more agents in solution with a carrier such as water and/or an organic liquid. Nerve conduits in accordance with embodiments of the invention may also incorporate one or more mats, sheets, powders, or fragments derived from the spun silica fibers without the additional agent(s).

In various embodiments, the additive may be added into the sol-gel, for example in liquid or encapsulated form, or as a slurry or mixture, prior to spinning of the silica fibers, and the as-spun fibers will incorporate the additive therein or thereon. In various embodiments, the additive is added into the sol-gel after at least a portion of the ripening time.

In other embodiments, the agent is incorporated onto the silica fiber mats after they are spun. After completion of the electrospinning process, the resulting mat is removed from the drum. For example, the mat may be cut and peeled away from the drum in one or more pieces. The mat may be cut to size, if desired or necessary, and the electrospun mat of silica fibers may be coated and/or infiltrated with one or more agents for use with or as a nerve conduit. For example, the agent may be deposited over the silica fibers via techniques such as spraying or misting of a solution containing one or more agents, with or without a separate carrier liquid. In various embodiments, the agent may be incorporated into the silica fibers before use in a patient. In various embodiments, the silica fibers or mat is processed into silica fiber powder, and the additive is deposited on the powder (via, e.g., any of the above techniques) and/or mixed with the powder.

In various embodiments, one or more of the additives (e.g., healing agents) is incorporated into the silica fibers (and/or other portions of the nerve conduit) after the nerve conduit containing and/or at least partially composed of the silica fibers (or a powder or sheet thereof) is implanted in a patient. The one or more agents may be incorporated into the silica fibers or nerve conduit one or more times during the nerve growth and regeneration process. For example, one or more of the agents may be directed to the silica fibers via an injection or a catheter implanted into the patient.

Suitable agents utilized with nerve conduits in accordance with embodiments of the invention may increase bioactivity and/or promote more rapid nerve growth and healing. Such agents may include, for example, nerve growth factor, extracellular matrix protein, glial cell-derived neurotrophic factor, vascular endothelial growth factor, fibroblast growth factor, stem cells, blast cells, epithelial cells, or Schwann cells.

FIG. 1A is a schematic cross-sectional diagram of a nerve conduit 100 in accordance with embodiments of the present invention. As shown, nerve conduit 100 is or includes a tubular or cylindrical construct sized and shaped to receive, via openings at opposing ends, a proximal nerve end 110 and a distal nerve end 120. Thus, nerve conduits in accordance with embodiments of the invention may have any of a range of lengths (i.e., longitudinal dimensions) and may be sized and shaped to accommodate the proximal nerve end 110, the distal nerve end 120, and the distance therebetween. In various embodiments, the nerve conduit 100 also includes within its interior volume a matrix 130 that includes, consists essentially of, or consists of silica fibers, a silica fiber mat or sheet (or portion thereof), and/or gel and/or dust and/or fragments from silica fibers. In various embodiments, the matrix 130 fills all or a portion of a medial portion of the nerve conduit 100. The matrix 130 may contact terminal portions of the proximal nerve end 110 and the distal nerve end 120, or there may be a gap between the matrix 130 and one or both nerve ends 110, 120. While the matrix 130 may occupy a significant portion of the internal volume of the medial portion of the nerve conduit 100, the matrix 130, typically being at least partially composed of silica fibers and/or portions thereof, defines sufficient porosity to allow nerve regeneration therethrough as the nerve ends 110, 120 heal and reconnect. Indeed, the large amount of surface area of matrix 130 facilitates the healing of the nerve and the growth of nerve tissue. In various embodiments, the matrix 130 includes, consists essentially of, or consists of silica fibers and/or a silica fiber mat or sheet (or portion thereof) in which the fibers are substantially oriented along the longitudinal direction within the nerve conduit 100 (i.e., the direction from nerve end 110 to nerve end 120). Such embodiments may facilitate more rapid healing and growth of tissue between the nerve ends 110, 120.

In various embodiments, all or a portion of the matrix 130 and/or of the body of the nerve conduit 100 may incorporate one or more healing factors, medicants, or other agents for facilitating nerve regeneration and repair. For example, all or a portion of the matrix 130 and/or of the external structure of the nerve conduit 100 may incorporate one or more of nerve growth factor, extracellular matrix protein, glial cell-derived neurotrophic factor, vascular endothelial growth factor, fibroblast growth factor, stem cells, blast cells, epithelial cells, Schwann cells, or other biological healing factor or medicant. Such agents may be applied to the matrix 130 before or after the matrix 130 is disposed within the nerve conduit 100.

In various embodiments, at least a portion of the matrix 130 may have the form of a gel in which the silica fibers and/or dust or fibrous fragments thereof are suspended. In other embodiments, at least a portion of the matrix 130 includes, consists essentially of, or consists of the fibers, dust, or fibrous fragments.

Figure 1B:
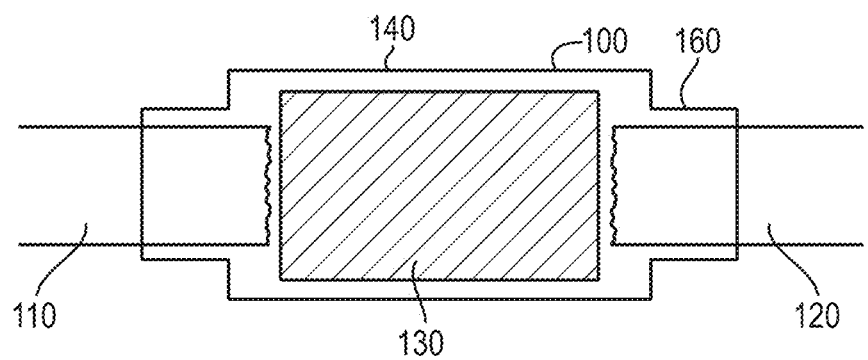
Figure 1C:
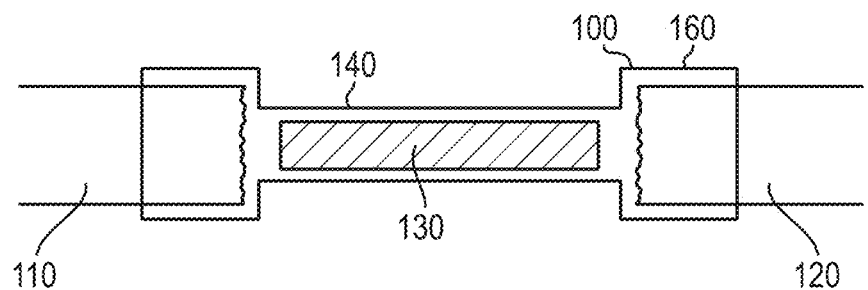

FIG. 1A depicts nerve conduit 100 as a tubular member having a substantially constant outer diameter. As shown in FIGS. 1B and 1C, in other embodiments the medial portion 140 of the nerve conduit 100 may have a larger or smaller outer diameter (and, in various embodiments, inner diameter) than one or both of the terminal portions 150, 160 of nerve conduit 100.

In various embodiments, the terminal portions of nerve ends 110, 120 may be attached (e.g., by suturing) to the terminal portions 150, 160 of nerve conduit 100 to ensure that they remain within the nerve conduit during nerve healing and regeneration. In other embodiments, the nerve ends 110, 120 are not attached to nerve conduit 100 and are merely inserted therewithin. In various embodiments, one or both of the nerve ends 110, 120 may penetrate into the nerve conduit by a distance ranging from, for example, approximately 1 mm to approximately 20 mm. Before the nerve ends 110, 120 are attached or and/or inserted within the nerve conduit 100, small terminal portions of one or both of the nerve ends 110, 120 may be removed (e.g., by cutting) to ensure that any tissue that may retard the healing and regeneration process (e.g., morbid or excessively damaged tissue) is removed.

In various embodiments, all or a portion of the nerve conduit 100 includes, consists essentially of, or consists of a polymeric material. For example, in various embodiments, the nerve conduit 100 may include, consist essentially of, or consist of one or more biocompatible polymers, e.g., polyesters, polyhydroxyalkonates, proteins, or polysaccharides. Exemplary polyhydroxyalkonates include poly(4-hydroxybutyrate), polyhydroxyvalerate, polyhydroxyhexanoate, polyhydroxyoctanoate, poly(3-hydroxybutyrate), poly(3-hydroxybutyric acid-co-3-hydroxyvaleric acid, and poly(3-hydroxybutyrate-co-3-hydroxyvalerate. Exemplary proteins include silk, collagen, gelatin, fibrinogen, elastin, and keratin. Exemplary polysaccharides include hyaluraonic acid, chitin, chitosan, and alginate. In various embodiments, all or a portion of the nerve conduit 100 may include, consist essentially of, or consist of, for example, silicone, polystyrene, polytetrafluoroethylene, polyglycolic acid, polyvinyl alcohol, or poly(L-lactide-co-ε-caprolactone). Such nerve conduits 100 may incorporate therewithin a matrix 130, at least a portion of which has the form of a gel in which silica fibers, a sheet thereof, and/or dust or fibrous fragments thereof are suspended. In other embodiments, at least a portion of the matrix 130 includes, consists essentially of, or consists of the fibers, sheet, dust, or fibrous fragments.

The nerve conduit 100 may be fabricated by any of a variety of different techniques, including molding, injection molding, casting, or machining. (For example, material may be removed from a precursor to the nerve conduit to thereby form the empty interior volume thereof; i.e., a solid cylinder may be formed or shaped, and then a portion of the interior volume may be removed to form a hollow tube). Such methods are conventional and may be performed by one of skill in the art without undue experimentation. In various embodiments, the polymeric material of nerve conduit 100 may be mixed with a silica fiber composition (e.g., silica fibers and/or powder and/or fibrous fragments thereof) prior to fabrication (e.g., when the polymeric material is in molten, liquid, semiliquid, or pelletized form), such that after fabrication the nerve conduit 100 includes, consists essentially of, or consists of a composite or mixture of the polymeric material and the silica fiber composition.

In other embodiments, all or a portion of the nerve conduit 100 includes, consists essentially of, or consists of silica fibers, e.g., all or a portion of a silica fiber mat. For example, a silica fiber mat and/or fragments or dust therefrom may be pressed around or in a mold having the desired shape and size of nerve conduit 100, and the mold may be removed thereafter. In various embodiments, water or another liquid may be applied to the silica fibers or fragments thereof while they are applied to the mold, and the mold is removed after the silica composition is at least partially dry (e.g., via evaporation of the liquid). Heat may be applied to speed evaporation of the liquid prior to mold removal. As mentioned above, the silica fibers or mat may be fabricated (e.g., by electrospinning) such that the fibers are substantially oriented in the same direction, e.g., the longitudinal direction spanning the nerve ends 110, 120.

Figure 1D:
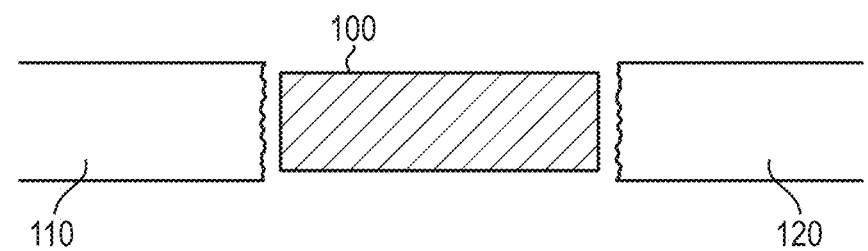
Figure 2A:
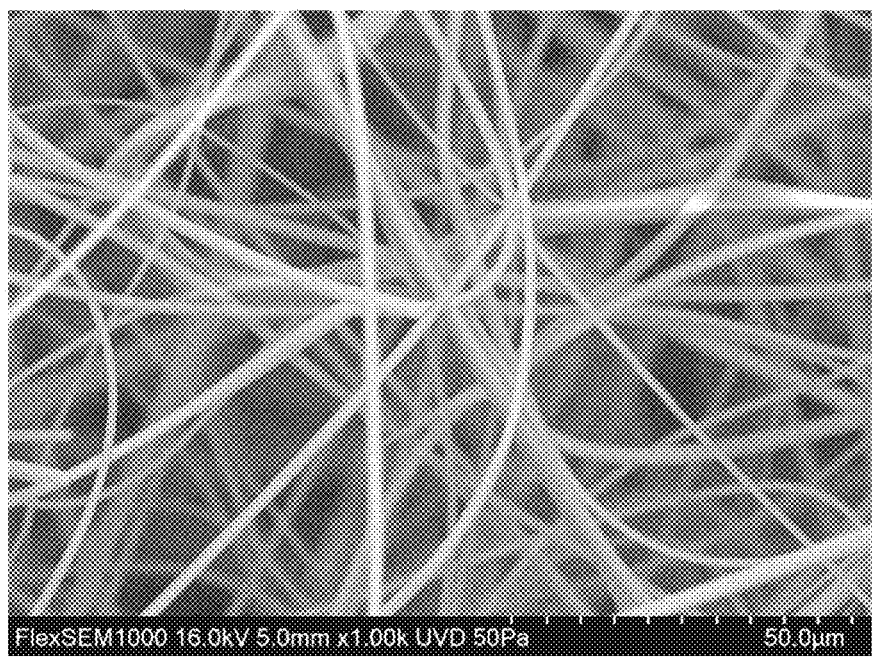
FIGS. 2A-2D are scanning electron microscopy (SEM) images of fibers spun in accordance with embodiments of the present invention. Images in FIGS. 2A-2D are at, respectively, 50, 100, 200, and 500 micron scale.
Figure 2B:
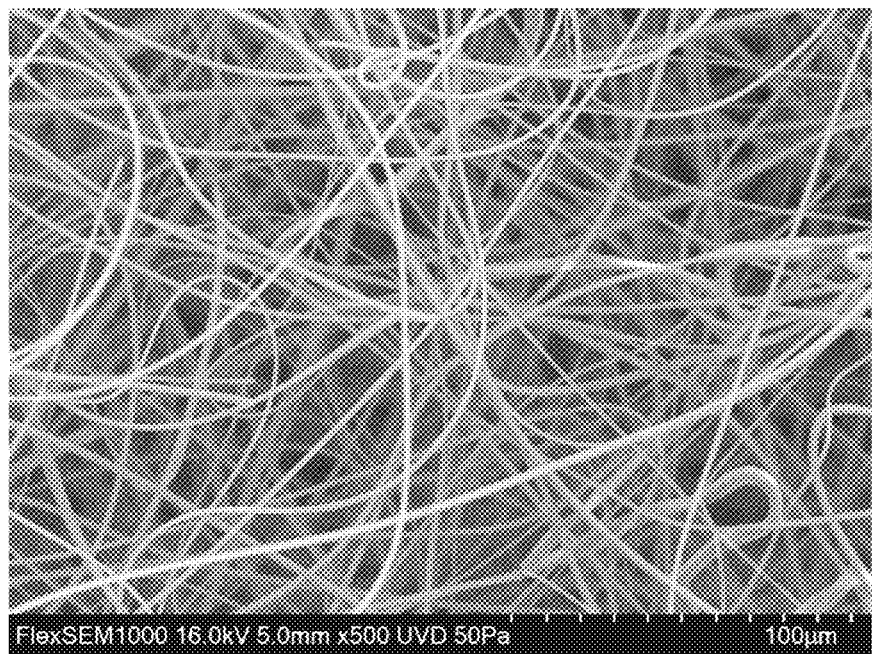
Figure 2C:
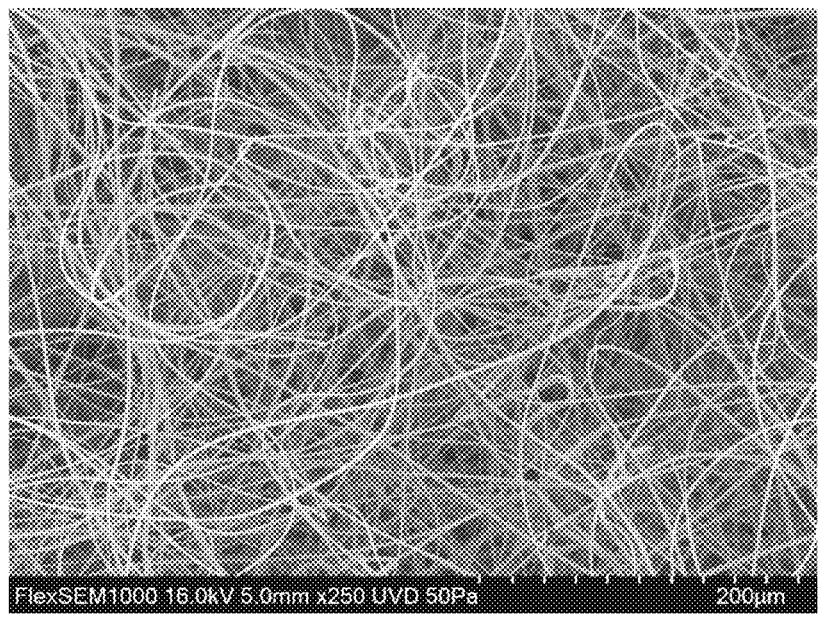
Figure 2D:
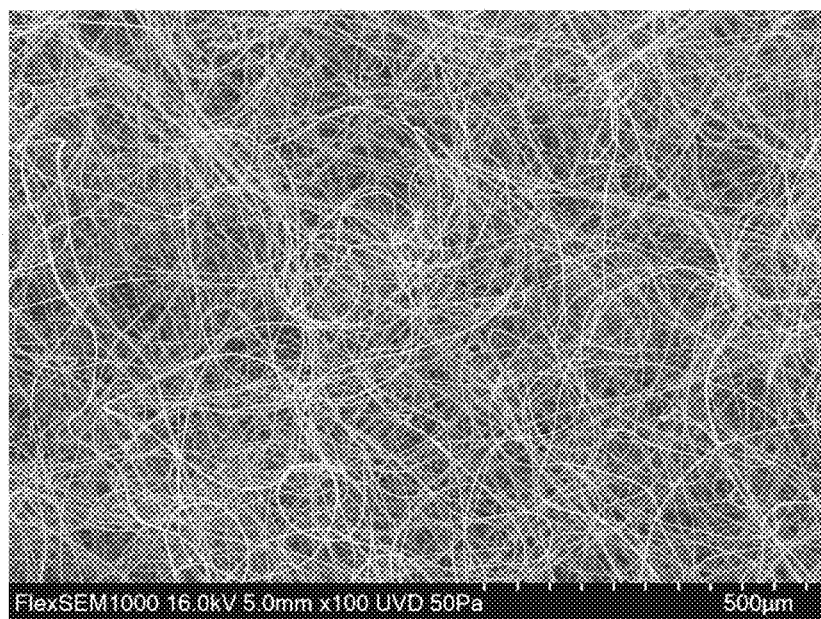

In yet other embodiments, all or a portion of the nerve conduit 100 may include, consist essentially of, or consist of silica fibers, e.g., all or a portion of a silica fiber mat or sheet, that do not necessarily define a tubular member with an interior volume. For example, as shown in FIG. 1D, all or a portion of the nerve conduit 100 may be a mat or sheet of silica fibers (which may be shaped substantially cylindrically) contacting or in close proximity to the nerve ends 110, 120. The porosity present in the silica fiber mat or sheet encourages nerve growth and regeneration through the nerve conduit. In such embodiments, the ends of the nerve conduit 100 may be attached to one or both of the nerve ends 110, 120, and/or the terminal portions of the silica fiber mat or sheet may slightly overlap the nerve ends 110, 120.

While embodiments of the invention have been described and illustrated as promoting nerve regeneration between two discrete nerve ends, for example, nerve ends formed due to severing of a nerve, embodiments of the invention may also be applied to nerves that are at least partially intact (e.g., damaged or partially transected). In such embodiments, the nerve conduit 100 may be partially or fully wrapped around the site of the nerve injury. For example, silica fibers or all or a portion of a silica fiber mat may be wrapped around the injury site. In various embodiments, the matrix 130 may be applied to the site of the injury before the nerve conduit 100 is applied.

EXAMPLES

Example 1: Preparation of Silica Fiber Mat

Silica fibers were prepared using an electrospinning process, in which a sol-gel was spun onto a collector drum to form a non-woven mat of fibers. The sol-gel was made in two parts. First, TEOS was mixed with ethanol, and then a second mixture containing HCl, water, and ethanol was titrated into the mixture. The sol-gel was then allowed to ripen for a few days under controlled conditions before spinning.

In one example, the first sol was made by weighing out 384 grams of TEOS 98% and 41.8 grams of anhydrous denatured ethanol, and pouring together. The first sol was allowed to let stand in a beaker, and a magnetic stirrer was used to create a homogenous solution. The second sol was made by weighing 41.8 grams of anhydrous denatured ethanol, 16.4 grams of distilled water, and 0.34 grams of hydrochloric acid, which was then poured together and mixed for 8 seconds with a magnetic stirrer until a homogenous second sol was formed.

The second sol was then poured into the titration device, which was placed above a beaker containing the first sol. The titration device then dripped about 5 drops per second until a third sol was formed via the mixing of the first sol and the second sol. During the dripping process, the first sol was continuously mixed with a magnetic stirrer while the second sol was dripped into the first sol.

The combined third sol was then placed into an enclosure box. A low pressure vacuum was provided by a fan on medium speed to remove fumes. The air temperature within the box was 72° F. with 60% humidity. The third sol was allowed to sit and process for about three days. The mixtures were agitated daily to reduce the build-up of crystalline structures. The third sol began to transition to sol-gel with evaporation of the alcohol solvent. Sol-gel may be monitored to determine an approximate amount of $C_2H_4$ (ethylene) in the vapors, which may be in the range of about 10-20% relative to that of the original sol before ripening. Upon proper gelatinization, the sol-gel was loaded into electrospinning machine or was frozen to preserve for electrospinning. In this example, proper gelatinization occurred when the total mass of the sol-gel was between about 70 grams and about 140 grams. This example may be scaled appropriately and the ranges may vary, yet still produce desirable structures. To further identify the ideal (or a desired) time to electropsin, portions of the gel may be dripped into the electric field of the spinning apparatus to evaluate the spinning properties of the sol-gel.

Figure 3:
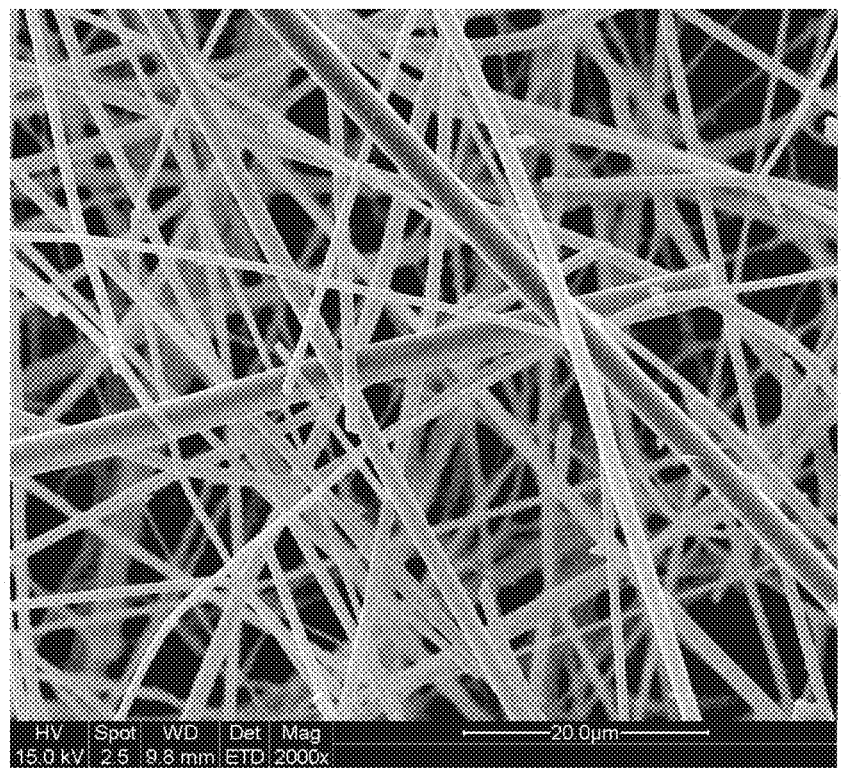
FIG. 3 shows an SEM image (20 micron scale is shown) of fibers spun in accordance with embodiments of the present invention after less ripening time than the figures shown in FIGS. 2A-2D.
Figure 4:
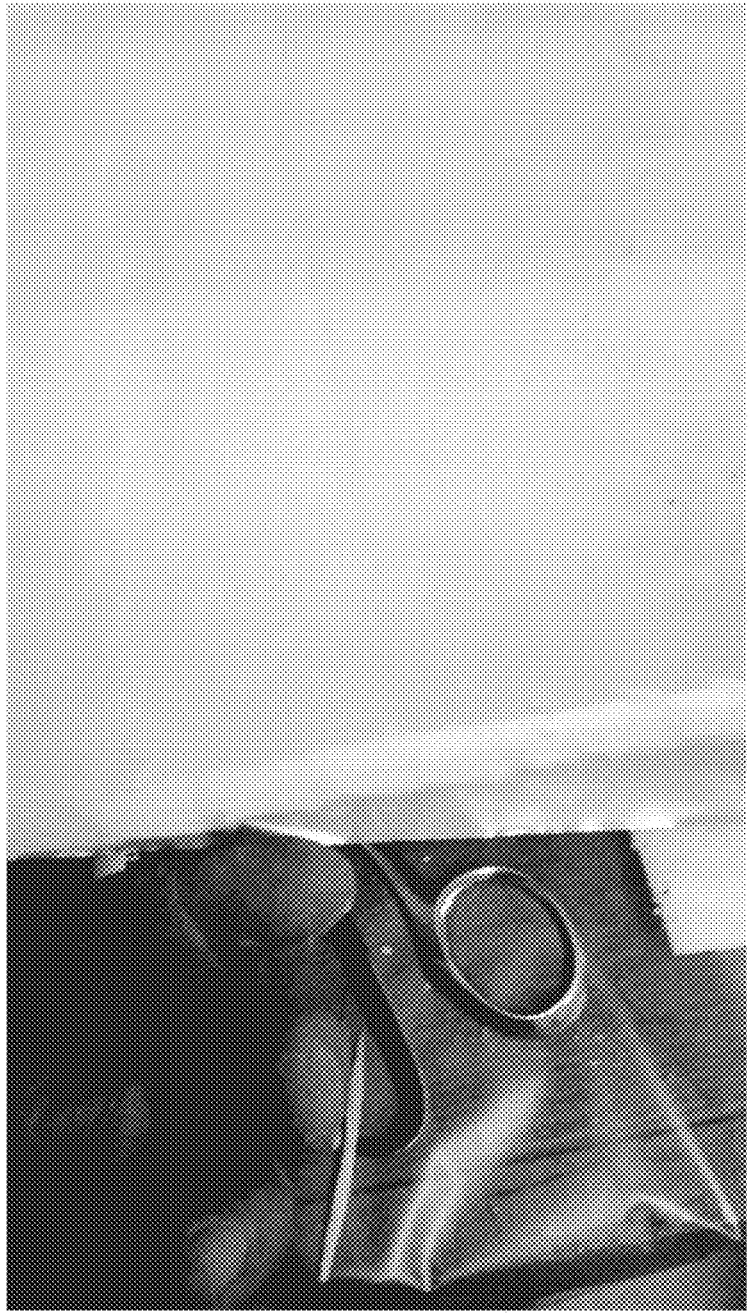
FIG. 4 shows a fiber mat spun with a thickness of about ¼ inch in accordance with embodiments of the present invention.

FIGS. 2A-2D are scanning electron microscopy (SEM) images of fibers spun in accordance with embodiments of the invention (50, 100, 200, and 500 micron scales shown). As shown, the fibers are flexible, smooth, dense, and continuous (not significantly fractured). FIG. 3 is an SEM image of fibers that were electrospun after less ripening time (20 micron scale shown), where the fibers are clearly rigid with many fractures clearly evident. Such fibers, in various embodiments, may be more brittle and more easily processed into silica fiber powder. FIG. 4 shows a fiber mat spun in accordance with embodiments of the invention. The flexibility and continuity of the fibers allows mats to be spun at a thickness of ¼ inch or more. The mat has a soft, flexible texture.

Figure 5A:
FIGS. 5A and 5B compare a silica fiber mat that was electrospun after a longer transitioning time in accordance with embodiments of the present invention (FIG. 5A), with a fiber mat electospun after a shorter transition time in accordance with other embodiments of the present invention (FIG. 5B).
Figure 5B:

FIGS. 5A and 5B are images depicting the variation of properties of silica fiber mats as a function of ripening time. The mat of FIG. 5A is illustrative of mats electrospun for at least 2-3 days in accordance with embodiments of the invention, while the mat of FIG. 5B is illustrative of mats electrospun after less ripening time. The material in FIG. 5A has a soft texture and is very flexible; such material may still be processed into fiber dust or used in sheet form. The material in FIG. 5B is brittle, inflexible, and thin, and may be easily processed into fiber dust.

Figure 6A:
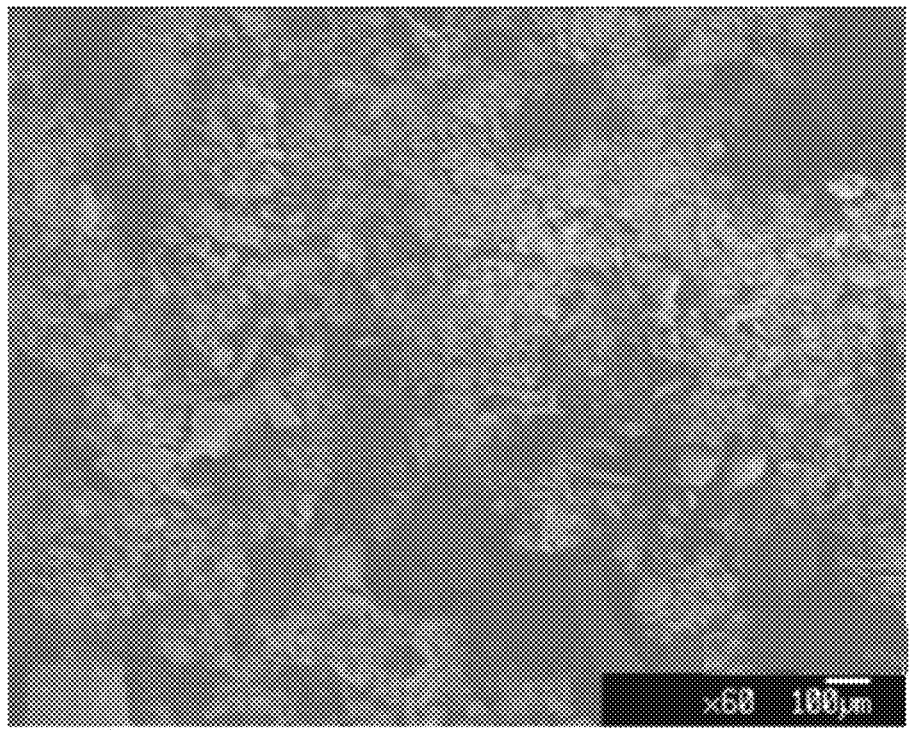
FIGS. 6A and 6B show SEM images of fiber dust in accordance with embodiments of the invention, with 100 μm scale shown.
Figure 6B:
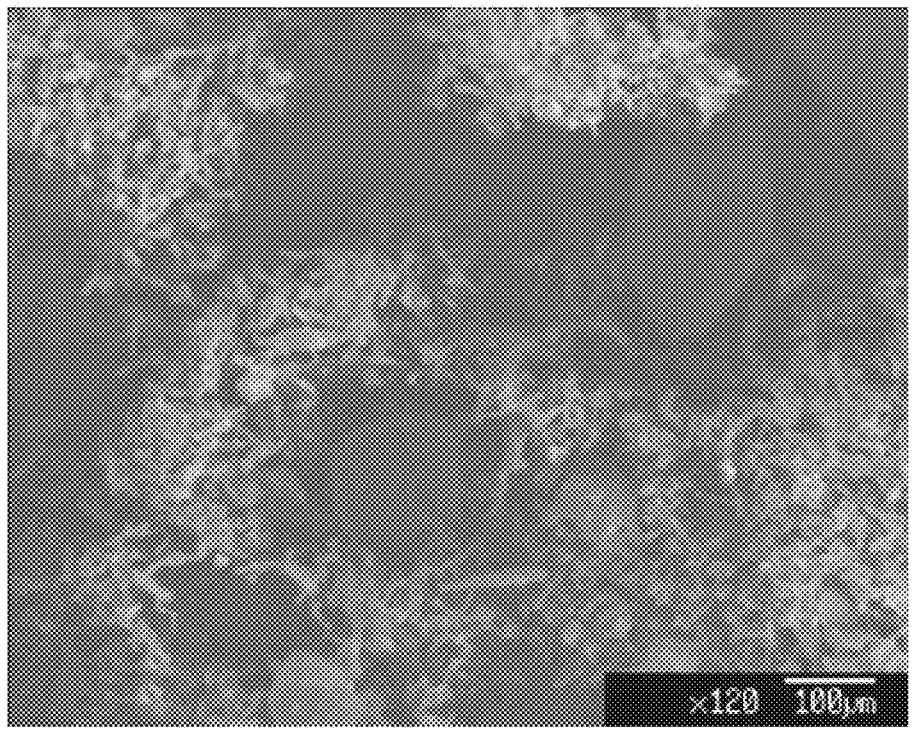

A silica fiber mat was fabricated and broken into fragments by rubbing through a series of screens of decreasing mesh size. The final screen was a 200 mesh screen, resulting in fiber dust and/or fibrous fragments having sizes of approximately 20 µm to approximately 200 µm. FIGS. 6A and 6B show SEM images of the resulting fiber dust, with 100 µm scale shown.

Once prepared, silica fiber mats were divided into portions for use in and as nerve conduits (e.g., as nerve conduits and/or at least a portion of the matrix thereof). In addition, fragments of silica fiber mats were either pressed into desired shapes and sizes for use in and as nerve conduits, or utilized in gels or other forms for use as at least portions of matrices of nerve conduits, or both.

The terms and expressions employed herein are used as terms and expressions of description and not of limitation, and there is no intention, in the use of such terms and expressions, of excluding any equivalents of the features shown and described or portions thereof. In addition, having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

The invention claimed is:

1. A method of fabricating an artificial nerve conduit, the method comprising:
  electrospinning a sol-gel to form a mat of silica fibers, wherein the sol-gel is produced, at least in part, by ripening, for at least 2 days at a humidity of 40% to 80% and a temperature of 50° F. to 90° F., an initial sol comprising 70% to 90% tetraethylorthosilicate (TEOS), 8% to 25% anhydrous ethanol, an acid catalyst, and water, wherein the initial sol is free of inorganic salts; and
  forming from at least a portion of the mat of silica fibers a tubular member defining a first opening configured to receive a first nerve portion and a second opening configured to receive a second nerve portion.

2. The method of claim 1, wherein forming the tubular member comprises pressing and/or molding the silica fibers and/or a powder derived from the silica fibers.

3. The method of claim 1, further comprising incorporating within and/or on at least a portion of the tubular member a healing agent.

4. The method of claim 3, wherein the healing agent comprises at least one of a growth factor, a matrix protein, or a plurality of cells.

5. The method of claim 4, wherein the healing agent comprises at least one of nerve growth factor, extracellular matrix protein, glial cell-derived neurotrophic factor, vascular endothelial growth factor, fibroblast growth factor, stem cells, blast cells, epithelial cells, or Schwann cells.

6. The method of claim 1, wherein the initial sol is ripened for at least 3 days.

7. The method of claim 1, wherein the sol-gel is electrospun when the weight of the sol-gel ranges from 10% to 60% of a starting weight of the initial sol prior to ripening.

8. The method of claim 1, wherein the sol-gel is electrospun when production of ethylene vapor therefrom ranges from 10% to 40% relative to the initial sol prior to ripening.

9. The method of claim 1, further comprising incorporating a healing agent into the sol-gel before electrospinning thereof, whereby the silica fiber mat comprises the healing agent incorporated therewithin.

10. The method of claim 1, further comprising incorporating a healing agent onto the silica fibers during electrospinning thereof.

11. The method of claim 1, further comprising incorporating a healing agent onto the mat of silica fibers after electrospinning thereof.

12. The method of claim 1, wherein the initial sol consists of TEOS, anhydrous ethanol, the acid catalyst, and water.

13. A method of fabricating an artificial nerve conduit, the method comprising:
forming from electrospun silica fibers a tubular member defining a first opening configured to receive a first nerve portion and a second opening configured to receive a second nerve portion,
wherein forming the tubular member comprises (i) electrospinning a sol-gel to form a mat of silica fibers, (ii) fragmenting the mat to form silica fiber powder, and (iii) pressing or molding at least a portion of the silica fiber powder.

14. The method of claim 13, wherein the fibers of the mat of silica fibers have diameters ranging from approximately 50 nm to approximately 5 μm.

15. The method of claim 13, wherein the fibers of the mat of silica fibers have diameters ranging from approximately 200 nm to approximately 1000 nm.

16. The method of claim 13, wherein the sol-gel is produced, at least in part, by ripening an initial sol comprising 70% to 90% tetraethylorthosilicate (TEOS), 8% to 25% anhydrous ethanol, an acid catalyst, and water.

17. The method of claim 13, further comprising incorporating a healing agent into the sol-gel before electrospinning thereof, whereby the silica fiber mat comprises the healing agent incorporated therewithin.

18. The method of claim 13, further comprising incorporating a healing agent onto the silica fibers during electrospinning thereof.

19. The method of claim 13, further comprising incorporating a healing agent onto the mat of silica fibers prior to fragmentation thereof.

20. The method of claim 13, further comprising, after fragmentation of the silica fiber mat, incorporating a healing agent onto the silica fiber powder.

21. An artificial nerve conduit fabricated according to claim 13.

22. The method of claim 16, wherein the initial sol is ripened for at least 2 days at a humidity of 40% to 80% and a temperature of 50° F. to 90° F.

23. The method of claim 22, wherein the initial sol is ripened for at least 3 days.

24. The method of claim 16, further comprising incorporating within and/or on at least a portion of the tubular member a healing agent.

25. The method of claim 24, wherein the healing agent comprises at least one of a growth factor, a matrix protein, or a plurality of cells.

26. The method of claim 24, wherein the healing agent comprises at least one of nerve growth factor, extracellular matrix protein, glial cell-derived neurotrophic factor, vascular endothelial growth factor, fibroblast growth factor, stem cells, blast cells, epithelial cells, or Schwann cells.

27. The method of claim 16, wherein the initial sol is free of inorganic salts.

28. The method of claim 16, wherein the initial sol consists of TEOS, anhydrous ethanol, the acid catalyst, and water.

29. A method of fabricating an artificial nerve conduit, the method comprising:
forming electrospun silica fibers at least in part by (i) producing a sol-gel from an initial sol comprising 75% to 90% TEOS, 8% to 25% ethanol, an acid catalyst, and water, and (ii) electrospinning the sol-gel, wherein the initial sol is free of inorganic salts; and
forming from the electrospun silica fibers a tubular member defining a first opening configured to receive a first nerve portion and a second opening configured to receive a second nerve portion,
wherein forming the tubular member comprises pressing the electrospun silica fibers and/or a powder derived from the electrospun silica fibers.

30. The method of claim 29, further comprising incorporating within and/or on at least a portion of the tubular member a healing agent.

31. The method of claim 30, wherein the healing agent comprises at least one of a growth factor, a matrix protein, or a plurality of cells.

32. The method of claim 30, wherein the healing agent comprises at least one of nerve growth factor, extracellular matrix protein, glial cell-derived neurotrophic factor, vascular endothelial growth factor, fibroblast growth factor, stem cells, blast cells, epithelial cells, or Schwann cells.

33. The method of claim 29, wherein producing the sol-gel comprises ripening the initial sol for at least 2 days at a humidity of 40% to 80% and a temperature of 50° F. to 90° F.

34. The method of claim 29, wherein the initial sol consists of TEOS, anhydrous ethanol, the acid catalyst, and water.

* * * * *